United States Patent [19]

de Jongh et al.

[11] Patent Number: 4,921,845
[45] Date of Patent: May 1, 1990

[54] 11-ARYLSTEROID COMPOUNDS

[75] Inventors: Hendrick Paul de Jongh, Hw Oss; Nicolaas P. van Vliet, Rhenen, both of Netherlands

[73] Assignee: Akzo N.V., Arnhem, Netherlands

[21] Appl. No.: 281,582

[22] Filed: Dec. 8, 1988

[30] Foreign Application Priority Data

Dec. 12, 1987 [NL] Netherlands .......................... 8703008

[51] Int. Cl.$^5$ ................... A61K 31/58; A61K 31/585; A61K 31/56; C07J 1/00
[52] U.S. Cl. ..................... 514/172; 514/173; 514/174; 514/175; 514/179; 540/17; 540/23; 540/107; 540/108; 552/612; 552/644; 552/647
[58] Field of Search ................ 260/397.45; 514/172, 514/173, 174, 175, 179; 540/17, 23, 107, 108

[56] References Cited

U.S. PATENT DOCUMENTS

| 4,386,085 | 5/1983 | Teutsch et al. | 260/397.45 |
| 4,447,424 | 5/1984 | Teutsch et al. | 260/397.1 |
| 4,519,946 | 5/1985 | Teutsch et al. | 260/397.1 |
| 4,609,651 | 9/1986 | Rohde et al. | 260/397.45 |
| 4,634,695 | 1/1987 | Torelli et al. | 514/178 |
| 4,780,461 | 10/1988 | Neef et al. | 260/397.45 |

FOREIGN PATENT DOCUMENTS 0190759 8/1986 European Pat. Off. .
2175905 12/1986 United Kingdom .

OTHER PUBLICATIONS

Chemical Abstracts; vol. 106 (1987) #84942B; Faustini et al.

Primary Examiner—Joseph A. Lipovsky
Attorney, Agent, or Firm—William M. Blackstone

[57] ABSTRACT

The invention relates to new 11-arylsteroid compounds, having a strong antiprogestin and a weak or nonexistent antiglucocorticoid activity, to processes for preparing said compounds and also to pharmaceutical preparations which contain these derivatives as active constituent, characterized in that said steroids have the following formula:

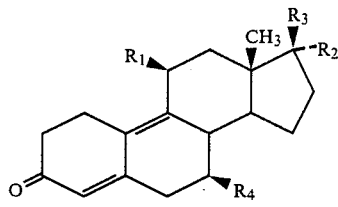

in which
$R_1$ is an aryl group with a

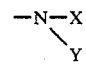

group as substituent, X and Y each being separately H or a (1–4 C) hydrocarbyl group or together a (2–C) hydrocarbyl group which forms a 3- to 7-membered ring together with the nitrogen atom;

$R_2$ is hydrogen, hydroxyl, an acyloxy or an alkoxy group or a saturated or unsaturated hydrocarbyl group containing 1–8 carbon atom-. which hydrocarbyl group is provided with at least one hydroxyl, oxo, azido, cyano and/or halogen group;

$R_3$ is a hydroxyl, an acyloxy or an alkoxy group or an acyl group optionally substituted by a hydroxyl, alkoxy, acyloxy or halogen group; or $R_2$ and $R_3$ together form a ring system, with the proviso that if $R_3$ is hydroxyl, $R_2$ is not hydrogen or hydroxyl; and $R_4$ is a methyl or ethyl group;

and the $\alpha$- and $\beta$-bonds are indicated by dashed (...) and wedged (◄) lines respectively.

11 Claims, No Drawings

11-ARYLSTEROID COMPOUNDS

The invention relates to new 11-arylsteroid compounds, to processes for preparing said compounds and also to pharmaceutical preparations which contain these derivatives as active constituent.

The antiprogestins include, inter alia, substances which have affinity for the progesterone receptor, such substances not exerting, or exerting to a considerably reduced extent, the action of progesterone. Progesterone is involved, inter alia, in the nidation of a fertilized egg cell in the uterus wall. It will be possible to prevent the nidation by occupying the receptor sites in the uterus cells with antiprogestins, as a result of which the pregnancy can be terminated at a very early stage. The antiprogestins further include progesterone synthesis inhibitors. Antiprogestins are known from the U.K. Patent Application GB 2175905 and PCT Patent Application WO 87/05908.

However, it has emerged that in addition to the desired antiprogestin activity, such antiprogestins also have an antiglucocorticoid activity which is undesirable if these substances are used as a pregnancy-terminating agent, as drug against endometriosis or as drug against steroid hormone dependent cancers, such as breast, endometrium and vagina cancer.

A new group of compounds has now been found which have a strong antiprogestin and a weak or nonexistent antiglucocorticoid activity.

The invention therefore relates to said steroids, characterized in that said steroids have the following formula:

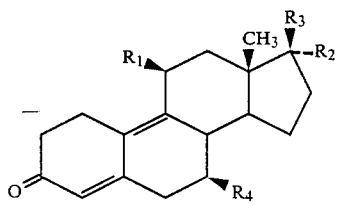

in which $R_1$ is an aryl group with a

group as substituent, X and Y each being separately H or a (1–4C) hydrocarbyl group or together a (2–6C) hydrocarbyl group which forms a 3- to 7-membered ring together with the nitrogen atom;

$R_2$ is hydrogen, hydroxyl, an acyloxy or an alkoxy group or a saturated or unsaturated hydrocarbyl group containing 1–8 carbon atoms, which hydrocarbyl group is provided with at least one hydroxyl, oxo, azido, cyano and/or halogen group;

$R_3$ is a hydroxyl, an acyloxy or an alkoxy group or an acyl group optionally substituted by a hydroxyl, alkoxy, acyloxy or halogen group; or $R_2$ and $R_3$ together form a ring system, with the proviso that if $R_3$ is hydroxyl, $R_2$ is not hydrogen or hydroxyl; and $R_4$ is a methyl or ethyl group;

and the $\alpha$- and $\beta$-bonds are indicated by dashed (---) and wedged (◂) lines respectively.

The aryl group in $R_1$ may be derived from, for example, benzene, biphenyl, naphthalene, anthracene or phenanthrene. A phenyl group is the most preferred. In the case of a phenyl group, the substituent is preferably in the meta or para position.

The substituent on the aryl group is a group having the formula

The (1–4C) hydrocarbyl group X and Y may be, inter alia, methyl, ethyl, vinyl, ethinyl, propyl, 2-propenyl, allenyl, 1-propynyl, butyl and branched analogues thereof. If X and Y together form a (2–6C) hydrocarbyl group, the hydrocarbyl group may be saturated or unsaturated; preferably the hydrocarbyl group contains 4 or 5 carbon atoms. Preferably, X and Y are a saturated alkyl group containing 1–3 carbon atoms and, with still more preference, methyl.

The (1–8C) hydrocarbyl group $R_2$ which is provided with at least one hydroxy, oxo, azido, cyano and/or halogen group may be, inter alia, 3-hydroxy-1-propynyl, 3-hydroxy-1-propenyl, chloroethinyl, bromoethinyl, 3-hydroxypropyl and methyloxymethyl. The acyloxy group $R_2$ and $R_3$ is preferably derived from an organic carboxylic acid containing 1–18 carbon atoms, such as acetic acid, propionic acid, butyric acid, trimethylacetic acid, phenylacetic acid, cyclopentylpropionic acid, phenylpropionic acid, valeric acid, caproic acid, pelargonic acid, lauric acid, palmitic acid, benzoic acid or succinic acid.

With the term alkoxy group in the definition of $R_2$ and $R_3$ is preferably meant an unsubstituted or substituted alkoxy group containing 1–12 carbon atoms, such as, for example, methoxy, ethoxy, cyclopentyloxy, benzyloxy and tetrahydropyranyloxy.

The acyl group $R_3$ optionally substituted by a hydroxyl, alkoxy, acyloxy or halogen group is preferably derived from an organic carboxylic acid containing 1–18 carbon atoms, such as those already mentioned above. Examples of suitable substituted acyl groups are hydroxyacetyl, fluoroacetyl, chloroacetyl and propionyloxyacetyl.

If $R_2$ and $R_3$ together represent a ring system, the preference is for heterocyclic 5- or 6-ring systems, the ring being bound to position 17 of the steroid skeleton by means of an oxygen atom which forms part of the ring. The greatest preference is for the following heterocyclic ring systems:

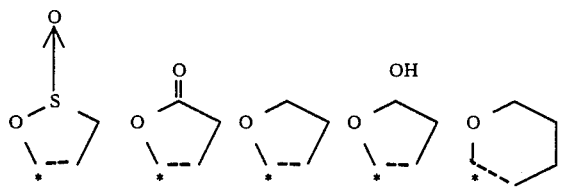

the carbon atom which is provided with an * being the carbon atom at position 17 of the steroid skeleton.

For $R_2$, the greatest preference is for a saturated or unsaturated alkyl group containing 1–4 carbon atoms substituted at least by one hydroxyl or oxo group and for $R_3$ it is for a hydroxy group, a (1–6C) acyloxy or a (1-6C) alkoxy group if $R_2$ and $R_3$ do not together form a ring system. With still more preference, $R_2$ is then an unsaturated alkyl group containing 1-4 carbon atoms and having 1 or 2 hydroxyl groups.

The invention also relates to pharmaceutical preparations which contain one ore more of the compounds according to the invention as active constituent. The new compounds may be administered in the usual manner orally, intravaginally or parenterally in combination with pharmaceutical auxiliary substances in the form of tablets, pills, dragees and other normal dispensing forms. The dosage forms may be prepared by known galenic procedures.

The compounds according to the present invention may be prepared starting from 7$\beta$-methyl-3,17-dioxoan-drost-4-en-19-al or an equivalent 7$\beta$-$R_4$ compound.

Said compounds are converted by analogy with the method for converting the corresponding 7$\alpha$-methyl compound into 17$\beta$-hydroxy-7$\alpha$-methyl-19-nor-17$\alpha$-pregn-5(10)-en-20-yn-3-one as described in Receuil des Traveaux Chimiques des Pays-Bas 105 (1986), 111-115, into 17$\beta$-hydroxy-7$\beta$-methyl-17$\alpha$-$R_2$-oestr-5(10)-en-3-one or an equivalent 7$\beta$-$R_4$ compound. After bromination and dehydrobromination, for example, with phenyltrimethylammonium tribromide and pyridine to the corresponding $\Delta^4$, $\Delta^9$-dienes, said compounds are ketalized to the $\Delta^{5(10)}$, $\Delta^{9(11)}$-3-ketal. The ketal group has the formula:

$R_5$ and $R_6$ representing an alkyl group containing 1-4 carbon atoms or $R_5$ and $R_6$ together forming an alkylene group containing 2-5 carbon atoms and * specifying the carbon atom in position 3 of the steroid skeleton. The ketalization can be carried out in an $R_5OH$ alcohol in the presence of an acid as catalyst; in this case, $R_6$ is identical to $R_5$. If the reaction is carried out in the presence of a diol, a ketal is obtained in which $R_5$ and $R_6$ together form an alkylene group.

Starting from said 3-ketal compounds, the group in position 11 can then be additionally introduced into the steroid skeleton.

Thus, after epoxidation of the $\Delta^{5(10)}$ double bond, for example with m-chloroperbenzoic acid in $CH_2Cl_2$ and $NaHCO_3$, the $R_1$ group can be introduced with the simultaneous formation of an OH group in position 5 and the rearrangement of the double bond from 9(11) to 9(10) by reaction with an $R_1$-metal-X compound containing $R_1$, X being a halogen atom, such as $R_1MgBr$, for example in the presence of CuCl in tetrahydrofuran or with an $R_1Li$ compound. After the introduction of $R_1$, dehydration and hydrolysis may be carried out immediately (for example), in 80% acetic acid at 75° C. or in 2N HCl in acetone); in that case, compounds are obtained which contain 17-$\alpha$-$R_2$ and 17$\beta$-OH.

If $R_2$ or $R_3$ is an OH group, said group may, if desired, be esterified or etherified by methods known per se before or after introducing the $R_2$ group or after dehydration and hydrolysis.

For the preparation of compounds in which $R_2$ and $R_3$ together form a ring system, the process proceeds analogously to the method already described, provided that $R_2$ is an oxygen-containing group in which the oxygen atom is protected by means of a hydrolysable group. The group used according to this variant an 17$\alpha$ is preferably an alkyl, alkenyl or alkynyl ether. The greatest preference is for groups having a terminal tetrahydropyranyl group. After introducing group $R_1$, unsaturated bonds optionally present in the group introduced at 17$\alpha$ are reduced if desired. Subsequently, dehydration and hydrolysis is carried out with the protective groups in the 17$\alpha$ substituent being split off simultaneously to form compounds containing 17$\beta$-OH, 17$\alpha$-$R_2$. In the step in which a part of the group introduced at 17$\alpha$ is split off, preferably the ether group and, with still more preference, the tetrahydropyranyl group is split off to form an alkyl, alkenyl or alkynyl group with a terminal hydroxy group. This group is finally cyclized with the 17$\beta$-OH group by processes known per se.

For the preparation of compounds according to the general formula, the starting point may be a 3-methoxy-7$\beta$-$R_5$-18-(13 C)-alkyloestra-1,3 5-trien-17$\beta$-ol. After Birch reduction (which yields $\Delta^2$, $\Delta^{5(10)}$), Oppenauer oxidation (which yields 17-keto) and reaction with a weak acid (which yields 3-keto, $\Delta^{5(10)}$), a compound is obtained having the formula as shown for compound 11 in the said Receuil paper, provided that 7$\alpha$-$CH_3$ is replaced by 7$\beta$-$R_4$ and that 13-$CH_3$ is replaced by 13-(2-4 C)alkyl.

Another method for the preparation of compounds according to the invention is that in which group $R_1$ is first introduced in position 11 and subsequently the functional groups are incorporated at 17. Starting from compounds having formula 11 in the Receuil paper, provided that 7$\alpha$-$CH_3$ is replaced by 7$\beta$-$R_4$ after ketalization to the 3-ketal as already described, the 17-keto group is protected, for example by reduction with sodium borohydride to a hydroxyl group. After deketalization, bromination, dehydrobromination, ketalization of the 3-keto group and epoxidation, group $R_1$ can be introduced in position 11. Subsequently, the 17-keto group is reformed by oxidation, after which the desired groups are introduced at 17$\alpha$ and 17$\beta$ in a manner known per se and as already described above. Finally, dehydration and hydrolysis has to be carried out.

The compounds according to the invention are obtained in that a compound having the formula:

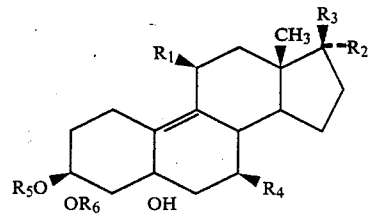

in which $R_1$, $R_2$, $R_3$, $R_4$, $R_5$, and $R_6$ have the same meaning as has already been described, provided that, if $R_2$ and/or $R_3$ represent an oxygen-containing group, $R_2$ and/or $R_3$ may also be an oxygen-containing group, the oxygen atom being protected by means of a hydrolysable group, is hydrolysed and dehydrated to form compounds according to the present invention. Preferably, the dehydration and the hydrolysis is carried out in one stage. The temperature at which said step is carried out is in general between 10° and 90° C.; the reaction time is usually 15 minutes to 4 hours. The dehydration/hydrolysis stage is carried out in a manner known per se and with agents known per se, such as, for example, with acetic acid or with HCl in acetone.

The invention is explained by reference to the following examples.

EXAMPLE 1 a. A solution of 13.7 g of sodium borohydride in a mixture of 130 ml of methanol and 18.5 ml of 1M sodium hydroxide solution was added dropwise at room temperature to a solution of 60 g of 7β-methyloestr-5(10)-ene-3,17-dione-3,3-dimethylacetal in 150 ml of tetrahydrofuran and a mixture of 75 ml of methanol plus 20 ml of 1M sodium hydroxide solution. After the reaction mixture had been stirred for 3 hours at room temperature, it was cooled to 0° C. and 75 ml of acetone was carefully added dropwise at a temperature of < +30° C. Then the reaction mixture was poured out into 800 ml of water. Extraction with methylene dichloride yielded an organic layer which was washed until neutral with water, dried on sodium sulphate, filtered and evaporated to dryness in vacuo. Yield: 60 g of crude 17β-hydroxy-7β-methyloestr-5(10)-en-3-one-3,3-dimethylacetal.

b. 30 g of the product obtained in step 2a were dissolved in a mixture of 150 ml of tetrahydrofuran and 100 ml of methanol. After adding a solution of 10 g of oxalic acid dihydrate in 50 ml of water plus 50 ml of methanol, stirring was carried out for 1½ hours at room temperature. Then the reaction mixture was poured out into a solution of 20 g sodium hydrogen carbonate in 6 l of water. Extraction with methylene dichloride yielded an organic layer which was washed with water, dried on sodium sulphate and evaporated to dryness in vacuo. After purification by chromatography on silica gel, 20 g of virtually pure 17β-hydroxy-7β-methyl-oestr-5(10)-en-3-one were obtained. Crystallization from ethanol yielded pure substance.

c. 24.2 g of this product was dissolved in 250 ml of dry pyridine. 32 g of phenyltrimethylammonium tribromide were then added scoopwise at room temperature. After stirring for 2 hours at room temperature, the reaction mixture was poured out in 1.1 l of ice water, to which 50 ml of concentrated sulphuric acid was added. The precipitate was filtered, washed until neutral with water and dried in vacuo. Yield: 21 g of 17β-hydroxy-7β-methyl-oestr-4,9-dien-3-one. 18 g of pure compound were obtained by crystallization from diethyl ether.

d. A suspension of 40 g of the product obtained in stage 2c and 0.4 g of p-toluenesulphonic acid in 150 ml of ethylene glycol and 60 ml of triethyl orthoformate was stirred for 2 hours at room temperature. Working up of the reaction mixture by neutralization with triethylamine and extraction with methylene dichloride yielded, after purification by chromatography on silica gel, 34.4 g of virtually pure 17β-hydroxy-7β-methyloestr-5(10),9(11)-dien-3-one-3-ethyleneacetal.

e. 11.6 g of solid sodium hydrogen carbonate and 15.8 g of m-chloroperbenzoic acid were added consecutively scoopwise at −35° C. to a cooled solution of 22 g of 17β-hydroxy-7β-methyloestr-5(10),9(11)-dien-3-one-3-ethyleneacetal in 350 ml of methylene dichloride. After being stirred for 1 hour at −35° C., the reaction mixture was diluted with a saturated sodium hydrogen carbonate solution followed by extraction with methylene dichloride. The organic layer was washed with 0.2M sulphite solution and with water until neutral, dried on sodium sulphate, filtered and evaporated to dryness in vacuo. After purification by chromatography through silica gel, 8.8 g of 5α,10α-epoxy-17β-hydroxy-7β-methyloestr-9(11)-en-3-one-3-ethyleneacetal were obtained.

f. 1.27 g of copper(I) chloride were added while stirring in a nitrogen atmosphere and at a temperature of −10° C. to a solution of p-dimethylaminophenylmagnesium bromide in dry tetrahydrofuran prepared from 3.1 g of magnesium turnings, 135 ml of dry tetrahydrofuran and 25.7 g of p-bromodimethylaniline. After stirring for 30 min. at −10° C., a solution of 11.8 g of 5α,10α-epoxy-17β-hydroxy-7β-methyloestr-9(11)-en-3-one 3-ethyleneacetal in 150 ml of dry tetrahydrofuran was added. The reaction mixture was stirred for 2½ hours at room temperature, then cooled to 0° C. and carefully decomposed with a saturated ammonium chloride solution. Extraction with methylene chloride yielded an organic layer which was washed until neutral with water, dried on sodium sulphate, filtered and evaporated to dryness in vacuo. After purification by chromatography on silica gel, 11.8 g of 11β-(4-dimethylaminophenyl)-5α-17β-dihydroxy-7β-methyloestr-9-en-3-one-3-ethyleneacetal were obtained.

g. 5 g of aluminium isopropylate were added while stirring and in a nitrogen atmosphere to a solution of 8.8 g of 11β-(4-dimethylaminophenyl)-5α-17β-dihydroxy-7β-methyloestr-9-en-3-one-3-ethyleneacetal in 50 ml of dry cyclohexanone and 335 ml of dry toluene.

After being stirred at reflux temperature for 2 hours, the reaction mixture was cooled to room temperature and a solution of 30 g of Seignette salt in 300 ml of water was added. Then the mixture was subjected to a steam distillation followed by extraction with methylene dichloride. The organic layer was washed until neutral with water, dried on sodium sulphate, filtered and evaporated to dryness in vacuo. After purification by chromatography on silica gel, 6.7 g of virtually pure 11β-(4-dimethylaminophenyl)-5α-hydroxy-7β-methyloestr-9-ene-3,17-dione-3-ethyleneacetal were obtained.

h. A solution of 21.0 g of propargyl alcohol tetrahydropyranyl ether in 120 ml of dry tetrahydrofuran was added dropwise in 15 minutes to a solution of ethylmagnesium bromide prepared from 3.0 g of magnesium turnings and 10.2 ml of ethyl bromide in 110 ml of dry tetrahydrofuran.

After stirring for 30 minutes, a solution of 13.9 g of 11β-(4-dimethylaminophenyl)-5α-hydroxy-7β-methyloestr-9-ene-3,17-dione-3-ethyleneacetal in 90 ml of dry tetrahydrofuran was added dropwise.

After being stirred for 3 hours at room temperature, the reaction mixture was poured out into 500 ml of a 10% NH$_4$Cl solution and extracted with methylene dichloride. The organic layer was washed until neutral with water, dried on sodium sulphate, filtered and evaporated to dryness in vacuo. After chromatography of the residue on silica gel, 13.4 g of 11β-(4-dimethylaminophenyl)-5α-17β-dihydroxy-7β-methyl-17α-(3-tetrahydropyranyloxy-1-propynyl)oestra-9-en-3-one-3-ethyleneacetal were obtained.

i. 13.4 g of the product obtained in stage 1h were dissolved in 200 ml of a 70% acetic acid solution and heated at 50° C. for 2½ hours. After neutralization with sodium hydrogen carbonate, extraction was carried out with methylene dichloride. The organic layers were washed until neutral, dried on sodium sulphate, filtered and evaporated to dryness in vacuo. Yield: 10.1 g of crude 11β-(4-dimethylaminophenyl)-17β-hydroxy-17α-(3-hydroxy-1-propynyl)-7β-methyloestra-4,9-dien-3-one. $[\alpha]_D^{20} = +352°$ (c=1, dioxane).

EXAMPLE 2

3.5 g of 11β-(4-dimethylaminophenyl)-17β-hydroxy-17α-(3-hydroxy-1-propynyl)-7β-methyloestra-4,9-dien-3-one were dissolved in 250 ml of absolute ethanol and hydrogenated in the presence of 2.8 g of Lindlar catalyst until 1 equivalent of hydrogen had been absorbed (1.5 hours). The catalyst was filtered off and the filtrate was evaporated to dryness in vacuo. After chromatographing on silica gel, 11β-(4-dimethylaminophenyl)-17β-hydroxy-17α-(3-hydroxy-1-(Z)-propenyl)-7β-methyloestra-4,9-dien-3-one was obtained. $[α]_D^{20} = +426°$ (c=1, dioxane).

EXAMPLE 3

A solution of 2 g of 11β-(4-dimethylaminophenyl)-17β-hydroxy-17α-(3-hydroxy-1-propynyl)-7β-methyloestra-4,9-dien-3-one in 200 ml of a 1/1 mixture of toluene and ethanol was hydrogenated in the presence of 200 ml of 5% Pd-BaSO4 until 2 equivalents of hydrogen had been absorbed. The catalyst was filtered off and the filtrate evaporated to dryness. Chromatography on silica gel yielded 11β-(4-dimethylaminophenyl)-17β-hydroxy-17α-(3-hydroxy-1-propyl)-7β-methyloestra-4,9-dien-3-one. $[α]_D^{20} = +404°$ (c=1, dioxane).

EXAMPLE 4

A solution of 10 g of 11β-(4-dimethylaminophenyl)-17β-hydroxy-17α-(3-hydroxy-1-propyl)-7β-methyloestra-4,9-dien-3-one in 200 ml of methylene dichloride was added to a stirred suspension of 15 g of pyridinium chlorochromate in 200 ml of methylene dichloride. The mixture obtained was stirred for 30 min. at 20° C., diluted with 400 ml of ether and filtered through hyflo. The filtrate was concentrated and chromatographed on silica gel. In this manner, 4.5 g of 11β-(4-dimethylaminophenyl)-17β-hydroxy-7β-methyl-17α-(3-oxopropyl)oestra-4,9-dien-3-one were obtained, very predominantly in the form of the cyclic hemiacetal. This product was dissolved in 400 ml of toluene and after 45 g of silver carbonate/Celite (Fetizon's reagent) had been added, it was boiled for 5 hours under reflux. Then 22.5 g of silver carbonate/Celite was again added and boiling was continued for 2 hours. The reaction mixture was cooled, filtered and evaporated to dryness. The residue was chromatographed on silica gel, 11β-(4-dimethylaminophenyl)-17β-hydroxy-7β-methyl-3-oxo-19-nor-17α-pregna-4,9-diene-21-carboxylic acid gamma-lactone being obtained. $[α]_D^{20} = +394°$ (c=1, dioxane); mp 145° C.

EXAMPLE 5

0.6 g of p-toluenesulphonyl chloride was added to a solution of 1.2 g of 11β-(4-dimethylaminophenyl)-17β-hydroxy-17α-(3-hydroxy-1-propyl)-7β-methyl-4,9-oestra-dien-3-one in 15 ml of pyridine. After stirring for 6 hours, 100 ml of water was added, after which the mixture obtained was extracted with ether. The extracts were washed 5 times with water, dried on anhydrous Na2SO4 and evaporated to dryness. The residue was chromatographed on silica gel using toluene/ethyl acetate 1/1. This yielded 0.7 g of pure 11β-(4-dimethylaminophenyl)-7β-methyl-4',5'-dihydrospiro[estra-4,9-diene-17,2'(3'H)-furan]-3-one. $[α]_D^{20} = +426°$ (c=1, dioxane); mp 154° C.

EXAMPLE 6

Analogous to Examples 1h, 1i and 3 was prepared: 11β-(4-dimethylaminophenyl)-17β-hydroxy-17α-(4-hydroxy-1-butyl)-7β-methyloestra-4,9-diene-3-one as an amorphous powder, $[α]_D^{20} = +376°$ (c=0,5, dioxane), through reaction of 11β-(4-dimethylaminophenyl)-5α-hydroxy-7β-methyloestr-9-ene-3,17-dione-2-ethyleneacetal and 4-tetrahydropyranyloxy-1-butynylmagnesiumbromide, followed by hydrogenation and acid treatment.

EXAMPLE 7

Analogous to example 6 was prepared 11β-(4-dimethylaminophenyl)-7β-methyl-3',4',5',6'-tetrahydrospiro[estr-4,9-diene-17,2'(2'H)-pyran]-3-one, $[α]_D^{20} = +408°$ (c=0,5, dioxane) from 11β-(4-dimethylaminophenyl)-17β-hydroxy-17α-(4-hydroxy-1-butyl)-7β-methyloestra-4,9-dien-3-one.

We claim:
1. An 11-Arylsteroid, characterized in that said steroid have the following structure:

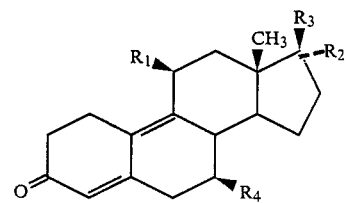

in which
R1 is an aryl group with a

group as substituent, X and Y each being separately H or a (1-4 C) hydrocarbyl group or together a (2-6 C) hydrocarbyl group which forms a 3- to 7-membered ring together with the nitrogen atom;
R2 is hydrogen, hydroxyl, an acyloxy or an alkoxy group or a saturated or unsaturated hydrocarbyl group containing 1-8 carbon atoms, which hydrocarbyl group is provided with at least one hydroxyl, oxo, azido, cyano or halogen group,
R3 is hydroxyl, an acyloxy or an alkoxy group or an acyl group optionally substituted by a hydroxyl alkoxy, acyloxy or halogen group; or R2 and R3 together form a ring system, with the proviso that if R3 is hydroxyl, R2 is not hydrogen or hydroxyl; and
R4 is a methyl or ethyl group;
and the α- and β-bonds are indicated by dashed (---) and wedged ( ) lines respectively.

2. Compound according to claim 1, wherein R1 is an aminophenyl group having the structure

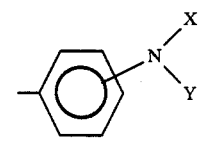

X and Y each separately representing a saturated alkyl group containing 1-3 carbon atoms.

3. Compound according to claim 1, wherein $R_2$ is a saturated or unsaturated alkyl group containing 1-4 carbon atoms substituted by at least one hydroxyl or oxo group.

4. Compound according to claim 1, wherein $R_2$ and $R_3$ form a 5- or 6-member ring system.

5. Compound according to claim 1, wherein $R_3$ is a hydroxyl group, a 1-6 C alkoxy group or a 1-6 C alkoxy group.

6. Compound according to claim 1, wherein $R_4$ is a methyl group.

7. Pharmaceutical preparation, comprising as the active constituent one or more compounds according to claim 1 in an amount effective to induce antiprogestin activity and a pharmaceutically acceptable carrier.

8. Method for preparing an 11-Arylsteroid having the following structure:

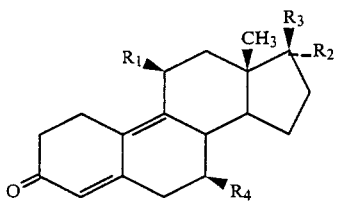

wherein
$R^1$ is an aryl group with

group as substituent, X and Y each being separately H or a (1-4 C) hydrocarbyl group or together a (2-6 C) hydrocarbyl group that forms a 3- to 7-membered ring together with the nitrogen atom;
$R^2$ is hydrogen, hydroxyl, an acyloxy or an alkoxy group or a saturated or unsaturated hydrocarbyl group containing 1-8 carbon atoms, which hydrocarbyl group is provided with at least one hydroxyl, oxo, azido, cyano or halogen group;
$R^3$ is hydroxyl, an acyloxy or an alkoxy group or an acyl group optionally substituted by a hydroxyl, alkoxy, acyloxy or halogen group, or $R_2$ and $R_3$ together form a ring system, with the proviso that if $R_3$ is hydroxyl $R_2$ is not hydrogen or hydroxyl; and
$R_4$ is a methyl or ethyl group;
and the $\alpha$- and $\beta$-bonds are indicated by dashed (---) and wedged (◂) lines respectively, comprising hydrolyzing a compound having the formula

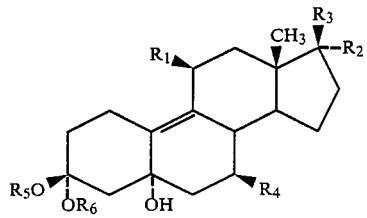

in which $R_1$, $R_2$, $R_3$ and $R_4$ have the same meaning as in claim 1, provided that, if $R_2$ or $R_3$ represent an oxygen-containing group, $R_3$ or $R_2$, respectively may also be an oxygen-containing group, wherein any oxygen atom in $R_2$ and $R_3$ is protected by means of a hydrolyzable group, and wherein $R_5$ and $R_6$ represent an alkyl group containing 1-4 carbon atoms or $R_5$ and $R_6$ together represent an alkylene group containing 2-5 carbon atoms, and dehydrating the product of hydrolysis to obtain the 11-Arylsteroid.

9. The method of claim 8, wherein hydroxyl groups are present at the position $17\alpha$ or $17\beta$ of the compound obtained.

10. The method of claim 9, wherein at least one of said hydroxyl groups at the $17\alpha$ or $17\beta$ position is esterified.

11. The method of claim 8, wherein a hydroxyl group is present at position $17\beta$ of the compound obtained, which is cyclized with an oxygen-containing group present at position $17\alpha$.

* * * * *